US012318567B2

(12) United States Patent
Nandipati et al.

(10) Patent No.: US 12,318,567 B2
(45) Date of Patent: Jun. 3, 2025

(54) PERFORATING CONNECTOR FOR MEDICAL FLUID CONTAINERS

(71) Applicants: BAXTER INTERNATIONAL INC., Deerfield, IL (US); BAXTER HEALTHCARE SA, Glattpark (CH)

(72) Inventors: Rajesh Nandipati, Karnataka (IN); Vandana Sakhare, Karnataka (IN)

(73) Assignees: Baxter International Inc., Deerfield, IL (US); Baxter Healthcare SA, Glatttpark (CH)

( * ) Notice: Subject to any disclaimer, the term of this patent is extended or adjusted under 35 U.S.C. 154(b) by 0 days.

(21) Appl. No.: 18/867,196

(22) PCT Filed: May 4, 2023

(86) PCT No.: PCT/US2023/021002
§ 371 (c)(1),
(2) Date: Nov. 19, 2024

(87) PCT Pub. No.: WO2023/224817
PCT Pub. Date: Nov. 23, 2023

(65) Prior Publication Data
US 2025/0114585 A1  Apr. 10, 2025

(30) Foreign Application Priority Data
May 20, 2022  (IN) .............................. 202241029132

(51) Int. Cl.
*A61M 39/04* (2006.01)
*A61M 39/22* (2006.01)
(52) U.S. Cl.
CPC ............ *A61M 39/04* (2013.01); *A61M 39/22* (2013.01)

(58) Field of Classification Search
CPC .................. A61M 39/04; A61M 39/22; A61M 2039/1027; A61M 2039/1072; A61M 39/1011; A61J 1/1475; F16L 37/0985
See application file for complete search history.

(56) References Cited

U.S. PATENT DOCUMENTS

2005/0283132 A1* 12/2005 Stanus ................ F16L 37/0985
604/403
2015/0297830 A1   10/2015 Tadashi

FOREIGN PATENT DOCUMENTS

EP  0 453 264       10/1991
WO  2007047845      4/2007

OTHER PUBLICATIONS

International Search Report—PCTUS2023/021002 dated Jul. 21, 2023—3 pages.
Written Opinion—PCTUS2023/021002 dated Jul. 21, 2023—p. 5 pages.

* cited by examiner

*Primary Examiner* — Theodore J Stigell
(74) *Attorney, Agent, or Firm* — K&L Gates LLP

(57) ABSTRACT

A perforating connector assembly including a valve; and a perforating connector comprising a perforator accepted by the valve, the perforator including a spiked end and a lever, the lever including a projection, a shell extending around the perforator and the valve, the shell including a pre-activation opening and a post-activation opening, a spring held compressed during pre-activation by a tab of the lever being located within the pre-activation opening, and an actuator slidingly engaged to the shell, the actuator including a projection, the actuator translatable by a user so that the projection becomes aligned with the tab located within the opening, wherein the user is able to push the projection into the pre-activation opening to disengage the tab from the (Continued)

opening, and wherein the spring is able to decompress and translate the perforator so that the medical fluid container is accessed and the tab becomes located within the post-activation opening.

20 Claims, 4 Drawing Sheets

PERFORATING CONNECTOR FOR MEDICAL FLUID CONTAINERS

PRIORITY CLAIM

The present application is a national phase entry of PCT Patent Application No. PCT/US2023/021002, filed on May 4, 2023, which claims priority to and the benefit of Indian Provisional Application No. 202241029132, filed on May 20, 2022, the entire contents of which are hereby incorporated by reference.

BACKGROUND

The present disclosure relates generally to medical fluid treatments and in particular to accessing fluid from a medical fluid container such as a peritoneal dialysis fluid bag.

Due to various causes, a person's renal system can fail. Renal failure produces several physiological derangeme3Ants. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid or PD fluid, into a patient's peritoneal chamber via a catheter. The PD fluid comes into contact with the peritoneal membrane in the patient's peritoneal chamber. Waste, toxins and excess water pass from the patient's bloodstream, through the capillaries in the peritoneal membrane, and into the PD fluid due to diffusion and osmosis, i.e., an osmotic gradient occurs across the membrane. An osmotic agent in the PD fluid provides the osmotic gradient. Used PD fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used PD fluid to drain from the patient's peritoneal cavity. The patient then switches fluid communication so that the patient catheter communicates with a bag of fresh PD fluid to infuse the fresh PD fluid through the catheter and into the patient. The patient disconnects the catheter from the fresh PD fluid bag and allows the PD fluid to dwell within the patient's peritoneal cavity, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

APD is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh PD fluid and to a fluid drain. APD machines pump fresh PD fluid from a dialysis fluid source, through the catheter and into the patient's peritoneal chamber. APD machines also allow for the PD fluid to dwell within the chamber and for the transfer of waste, toxins and excess water to take place. The source may include multiple liters of dialysis fluid, including several solution bags.

APD machines pump used PD fluid from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

Any of the above treatment modalities may operate with premade, e.g., bagged, solutions. Bagged solutions are typical for any type of PD (CAPD or APD). A bagged solution may also be used for HD, especially HHD (see for example U.S. Pat. No. 8,029,454 assigned to the assignee of the present application). Continuous renal replacement therapy ("CRRT") is an acute form of HD, HF or HDF and typically uses bagged dialysis fluids.

Premade, e.g., bagged, solutions for any of the above modalities are typically sterilized after filling and then capped to maintain the medical fluid in a sterilized condition until use. There are different ways to access the sterilized solutions at the time of use. One way is to spike or perforate a connector of the bag at the time of use, establishing medical fluid flow between the bag and a use point, such as a patient or disposable cassette.

There are issues appearing with existing bag perforating connectors. One container using an existing perforating connector is showing issues relating to the activation and piercing the film of the container or bag. The root cause analysis ("RCA") of failures over multiple years of use in the field shows that issues are due mainly to a lack of application of the right perforation force, in the right way, and at the right speed by the user, stiffness of the film, and weakness of the existing perforating connector material/design.

A need exists accordingly for an improved perforating connector.

SUMMARY

The present disclosure involves the use of a perforating connector assembly for accessing the medical fluid or solution located within a solution container or bag operable with any type of dialysis treatment, including any type of peritoneal dialysis ("PD") treatment, hemodialysis ("HD") treatment, hemofiltration ("HF") treatment, hemodiafiltration ("HDF") treatment or continuous renal replacement therapy ("CRRT") treatment. It should be appreciated that the perforating connector of the present disclosure may be used in any type of medical treatment having a bagged or otherwise stored medical fluid, which needs to be opened aseptically for use. The perforating connector may therefore be used additionally with any type of bagged medical infusion or intravenous fluid, saline, lactated ringers, etc.

The perforating connector assembly in one embodiment includes a valve for operation with the perforating connector, wherein the valve may be a flexible plastic or rubber piece that is welded, e.g., ultrasonically sealed, heat sealed, or solvent bonded to the medical fluid, e.g., PD fluid, bag. The valve may be a cylindrical plastic or rubber piece that has a circular flanged bottom, for increasing the welding surface for fluid-tight sealing to the bag.

The perforating connector includes a perforator/spike in one embodiment, which is fitted or formed with an o-ring that provides a sealed and moveable communication within the valve, so that medical, e.g., PD fluid, once accessed cannot flow from the bag, within the valve and around the outside of the perforator/spike. The perforator/spike is actuated within the valve to pierce the medical fluid, e.g., PD fluid, bag and access the medical or PD fluid.

The perforating connector further includes a shell, e.g., a cylindrical shell in one embodiment, which resides on the outside of the valve and the perforator/spike and centers/aligns movement of the perforator/spike within the valve. The shell is formed, e.g., molded, with a pair of openings. The perforator/spike includes an elongated cylindrical body, one end of which is the spiked end, the other end of which includes a connector for connecting to a tube, such as a flexible tube for carrying medical, e.g., PD fluid, from the perforating connector. A lever extends from the elongated tubular body, e.g., is molded with the tubular body. The lever in one embodiment extends from circular lever wall, which in turn extends from the elongated tubular body.

A tab is provided at the end of the lever and extends outwardly. The tab of the lever of the perforator/spike resides initially (before activation) in a pre-activation opening of the shell. Such engagement prevents the perforator/spike from moving or being moved relative to the shell valve or medical fluid, e.g., PD fluid, bag. The second or post-activation opening of the shell sets and end-of-travel location for the perforator/spike. Here, the tab resides in the post-activation opening of the shell after activation (bag spiking).

The perforating connector in one embodiment includes a compression spring, which is compressed initially between the circular lever wall of the perforator/spike and an internal ledge of the shell provided at or near a distal end of the shell. The spring is sized, e.g., with a coil diameter, such that it provides enough force upon decompression to cause the perforator/spike to pierce the PD fluid bag. When the tab on the lever of the perforator/spike is pushed beneath and out of the initial or pre-activation opening of the shell, the spring is able to uncoil and translate the perforator/spike.

The perforating connector of the present disclosure additionally includes an actuator or slider that is press-fitted into and thus constrained by slots provided in the shell so as to be able to only translate back and forth in one direction. The slots are provided in one embodiment by a member that extends radially outwardly from the shell. The actuator or slider may then include inwardly extending legs that engage the slots formed by the member, to hold the slider slidingly engaged to the shell. The actuator or slider is in one embodiment elongated so that its end covers the pre-activation opening formed in the shell that houses the outwardly extending tab of the lever of the perforator/spike in the pre-actuated condition or state. In this manner, the actuator or slider prevents (i) the user from prematurely actuating the perforating connector assembly and (ii) the outwardly extending tab from being moved prematurely, e.g., during shipping. The actuator or slider is further provided, e.g., molded, with a downwardly extending projection, which extends from a middle or off-center portion of the actuator or slider. The downwardly extending projection is used to push the outwardly extending tab of the lever from the pre-activation opening.

Any of the components of the perforating connector assembly of the present disclosure may be formed, e.g., molded, from a thermoplastic, such as polyetherimide ("PEI"), polyethersulfone ("PES"), polyamide/nylon ("PA"), acrylonitrile butadiene styrene ("ABS"), polycarbonate ("PC"), polyetheretherketone ("PEEK") or polyvinylchloride ("PVC"). The valve and/or an o-ring if provided separately may be formed, e.g., molded, alternatively from an elastomer, such as ethylene propylene diene monomer ("EPDM") rubber, neoprene rubber, silicon rubber, thermoplastic vulcunizates ("TPVs") or thermos-plastic elastomers ("TPEs"). The compression spring may be formed from a suitable spring metal so as to provide a desired amount of opening force.

Activation of the spring-activated perforating connector assembly occurs as follows in one embodiment. Prior to activation, the outwardly extending tab of the perforator/spike resides within the pre-activation shell opening, which prevents the pre-coiled spring from uncoiling and the perforator/spike from being translated relative to the rest of the assembly. Here, the sharp end of the piecing tip of the spike resides essentially at the base of the valve. Important in one embodiment is that the distal end of the actuator or slider is extended so that it covers and shields the tab of the perforator/spike residing within the pre-activation shell opening, preventing premature activation.

During activation of the perforating connector assembly, the user touches and translates the actuator or slider so that its downwardly extending projection meets the upwardly extending tab of the perforator/spike residing within the pre-activation shell opening. The user then presses the projection into the pre-activation opening, which forces the perforator/spike tab out of the opening, which in turn allows the spring to uncoil, translating the perforator/spike including the lever in a direction so that the spiked end of the perforator/spike pierces the medical fluid, e.g., PD fluid, bag open, allowing access to the medical or PD fluid within. During activation, the uncoiling spring translates the perforator/spike until the tab on the lever of the perforator/spike meets the post-activation shell opening. When this happens, the lever which is biased to spring upwardly during activation automatically snaps into the post-activation opening, preventing the perforator/spike from being translated further.

After activation of the perforating connector assembly, with the medical fluid, e.g., PD fluid, bag punctured, medical fluid or PD fluid may flow from the medical or PD fluid bag, through an internal lumen of the perforator/spike, into a medical or PD treatment fluid line. The outwardly extending tab of the lever arm of the of the perforator/spike remains within the post-activation shell opening, so that the spiked end of the perforator/spike continues to extend into the medical or PD fluid bag while the bag is emptied.

In light of the disclosure set forth herein, and without limiting the disclosure in any way, in a first aspect, which may be combined with any other aspect, or portion thereof, a perforating connector assembly includes a valve for sealing to a medical fluid container; and a perforating connector comprising a perforator sealingly accepted by the valve, the perforator including a spiked end and a lever, the lever including a tab, a shell extending around the perforator sealingly accepted by the valve, the shell including a pre-activation opening and a post-activation opening, a spring held compressed during pre-activation by the tab of the lever of the perforator being located within the pre-activation opening of the shell, and an actuator slidingly engaged to the shell, the actuator including a projection, the actuator configured to be translated by a user so that the projection becomes aligned with the tab located within the pre-activation opening, wherein the user is then able to push the projection into the pre-activation opening to disengage the tab from the pre-activation opening, and wherein the spring is then able to decompress and translate the perforator so that the medical fluid container is pierced open by the spiked end and the tab becomes located within the post-activation opening.

In a second aspect of the present disclosure, which may be combined with any other aspect, or portion thereof, the valve includes a flanged bottom for enhancing a weld between the valve and the medical fluid container.

In a third aspect of the present disclosure, which may be combined with any other aspect, or portion thereof, the perforator is sealingly accepted by the valve via an o-ring, and wherein the o-ring is formed with the perforator, the valve or is a separate o-ring.

In a fourth aspect of the present disclosure, which may be combined with any other aspect, or portion thereof, an end of the perforator includes a connector for connecting to a tube configured to transport medical fluid from the medical fluid container.

In a fifth aspect of the present disclosure, which may be combined with any other aspect, or portion thereof, the perforator includes an elongated cylindrical body and a circular wall extending from the body, wherein the lever extends from the circular wall, and wherein the spring is held compressed by the circular wall.

In a sixth aspect of the present disclosure, which may be combined with any other aspect, or portion thereof, the shell includes an internal ledge, and wherein the spring is also held compressed by the internal ledge.

In a seventh aspect of the present disclosure, which may be combined with any other aspect, or portion thereof, a distal end of the actuator is extended such that during pre-activation, the distal end covers the tab of the lever of the perforator located within the pre-activation opening of the shell.

In an eighth aspect of the present disclosure, which may be combined with any other aspect, or portion thereof, the tab extends radially outwardly from the lever into the pre- and post-activation openings.

In an ninth aspect of the present disclosure, which may be combined with any other aspect, or portion thereof, the lever is bent by the tab contacting an inner surface of the shell while the lever is moved between the pre- and post-activation openings, the bending of the lever biasing the lever to snap into the post-activation opening upon reaching the post-activation opening.

In a tenth aspect of the present disclosure, which may be combined with any other aspect, or portion thereof, the projection extends radially inwardly from the actuator to allow the user to push the projection into the pre-activation opening to disengage the tab from the pre-activation opening.

In an eleventh aspect of the present disclosure, which may be combined with any other aspect, or portion thereof, the shell includes an outwardly extending member defining at least one slot, and wherein the actuator includes at least one leg configured to engage the at least one slot so that the actuator is constrained to translate relative to the shell.

In a twelfth aspect of the present disclosure, which may be combined with any other aspect, or portion thereof, a perforating connector includes a perforator including a spiked end and a lever, the lever including a tab; a shell extending around the perforator, the shell including a pre-activation opening and a post-activation opening; a spring held compressed during pre-activation by the tab of the lever of the perforator being located within the pre-activation opening of the shell; and an actuator slidingly engaged to the shell, the actuator including a projection, the actuator configured to be translated by a user so that the projection becomes aligned with the tab located within the pre-activation opening, wherein the user is then able to push the projection into the pre-activation opening to disengage the tab from the pre-activation opening, and wherein the spring is then able to decompress and translate the perforator so that the medical fluid container is pierced open by the spiked end and the tab becomes located within the post-activation opening.

In a thirteenth aspect of the present disclosure, which may be combined with any other aspect, or portion thereof, the actuator resides radially adjacent the shell, such that the actuator is prone not to become entangled with an outside structure.

In a fourteenth aspect of the present disclosure, which may be combined with any other aspect, or portion thereof, at least one of a coil diameter and a material of the compression spring are selected so that the compression spring provides enough force for the medical fluid container to be pierced open by the spiked end of the perforator.

In a fifteenth aspect of the present disclosure, which may be combined with any other aspect, or portion thereof, the projection is provided at a middle or off-center portion of the actuator or slider.

In a sixteenth aspect of the present disclosure, which may be combined with any other aspect, or portion thereof, a method for accessing a medical fluid includes providing a perforator including a spiked end and a lever, the lever including an outwardly extending tab; providing a shell extending around the perforator, the shell including an opening holding the tab of the lever prior to accessing the medical fluid; providing a spring that is compressed by the perforator and the shell prior to accessing the medical fluid; and providing an actuator that enables a user to translate the actuator relative to the shell so that an inwardly extending projection of the of the actuator comes into registry with the tab of the lever held in the opening of the shell, wherein the user is able to push the actuator so that the projection removes the tab from the opening, allowing the spring to decompress and translate the perforator so that a medical fluid container is pierced open perforator.

In a seventeenth aspect of the present disclosure, which may be combined with any other aspect, or portion thereof, the method includes providing a valve with the medical fluid container, wherein the perforator moves sealingly within the valve.

In an eighteenth aspect of the present disclosure, which may be combined with any other aspect, or portion thereof, the shell extends around an outside of the valve.

In a nineteenth aspect of the present disclosure, which may be combined with any other aspect, or portion thereof, the medical fluid container is a PD fluid container.

In a twentieth aspect of the present disclosure, which may be combined with any other aspect, or portion thereof, the method includes preventing the actuator from being translated relative to the shell in a non-registry direction and releasably preventing the actuator from being translated relative to the shell in a registry direction.

In a twenty-first aspect of the present disclosure, which may be combined with any other aspect, or portion thereof, any of the features, functionality and alternatives described in connection with any one or more of FIGS. 1 to 10 may be combined with any of the features, functionality and alternatives described in connection with any other of FIGS. 1 to 10.

In light of the above aspects and the present disclosure set forth herein, it is accordingly an advantage of the present disclosure to provide a perforating connector having an actuator or slider advanced by the user, which does not extend radially far from the shell, which helps against premature activation and damage to the slider during shipping and prior to use.

It is another advantage of the present disclosure to provide a perforating connector having an actuator or slider advanced by the user, which is extended prior to use to cover an opening used to translate the perforator or spike, further preventing premature activation.

It is a further advantage of the present disclosure to provide a perforating connector that uses a spring force to perforate or spike a medical fluid container or bag, so that the user is not required to overcome the container or bag's piercing resistance.

It is yet another advantage of the present disclosure to provide a perforating connector having a defined end of travel for the actuator or slider advanced by the user.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description.

Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
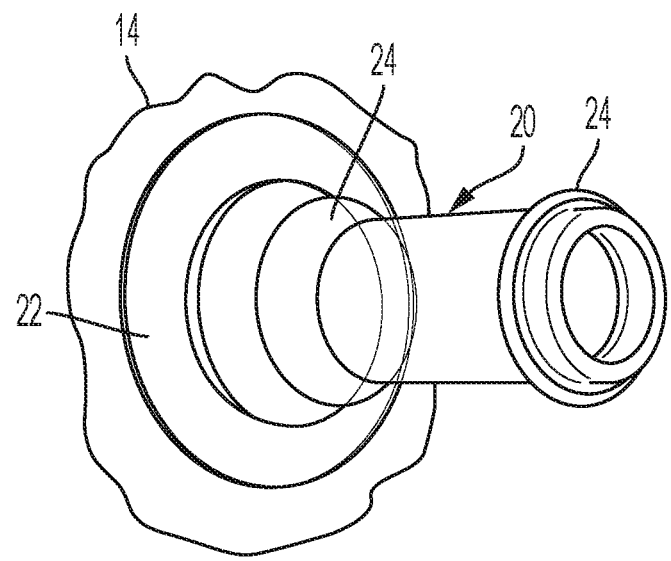
FIG. 1 is a perspective view of one embodiment of a valve for operation with the perforating connector of the present disclosure.

Referring now to the drawings and in particular to FIGS. 1 to 9, one embodiment for a perforating connector assembly 10 for use with a medical fluid container or bag 14 is illustrated. Perforating connector assembly 10 may be operable with any type of dialysis treatment including any type of peritoneal dialysis ("PD") treatment, hemodialysis ("HD") treatment, hemofiltration ("HF") treatment, hemodiafiltration ("HDF") treatment or continuous renal replacement therapy ("CRRT") treatment. It should be appreciated that perforating connector assembly 10 may be used alternatively in any type of medical treatment that uses a bagged or otherwise stored medical fluid, which needs to be opened aseptically for use. Perforating connector assembly 10 may therefore be used additionally with any type of bagged medical infusion, including intravenous fluids or drugs, saline, lactated ringers, etc.

Figure 6:
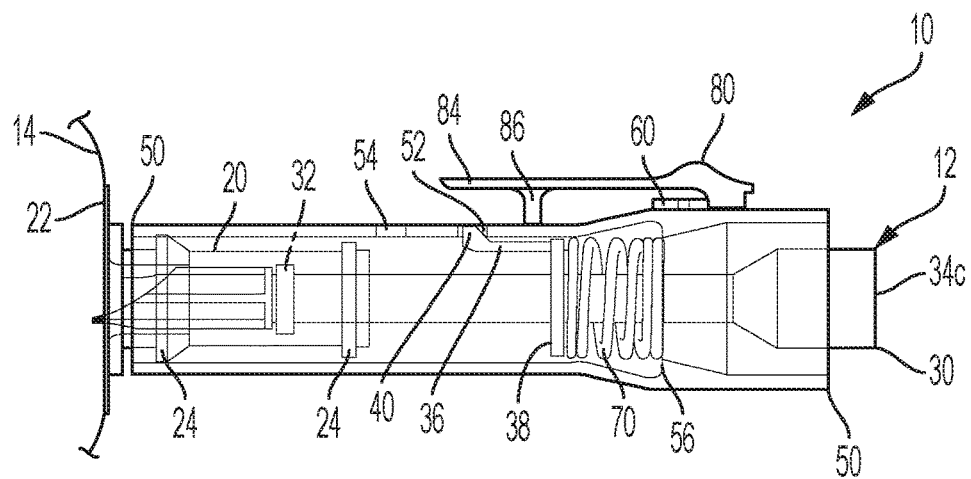
FIG. 6 is a side view illustrating one embodiment for the perforating connector assembly of the present disclosure in a pre-activation condition or state.
Figure 7:
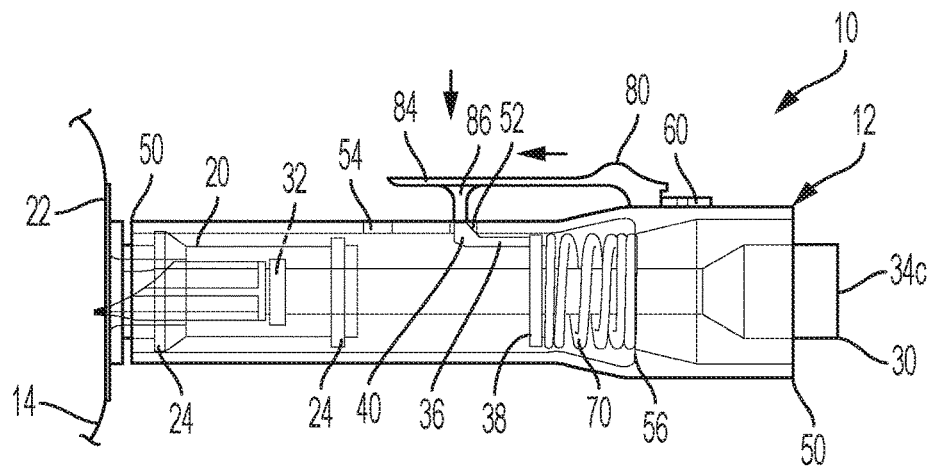
FIG. 7 is a side view illustrating one embodiment for the perforating connector assembly of the present disclosure during activation.
Figure 8:
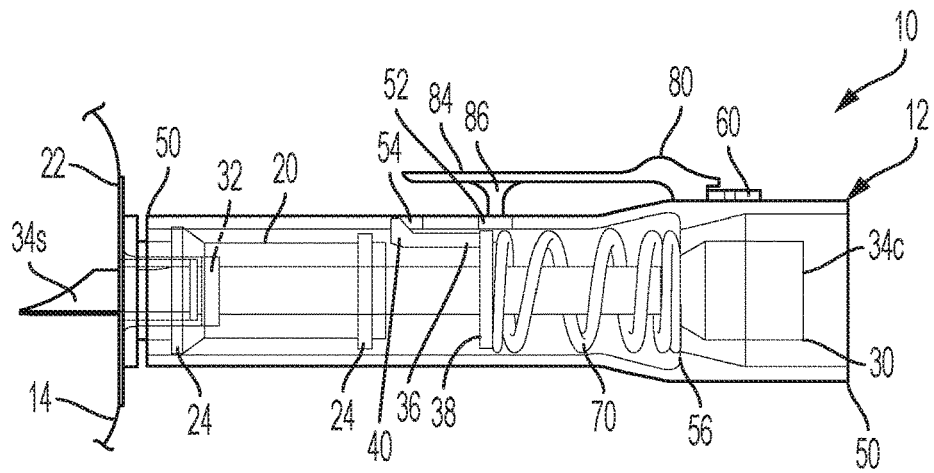
FIG. 8 is a side view illustrating one embodiment for the perforating connector assembly of the present disclosure in a post-activation condition or state.

FIGS. 6 to 8 illustrate that perforating connector assembly 10 in one embodiment includes a perforating connector 12 that operates with a valve 20, which is sealed to a medical fluid container or bag 14. Perforating connector 12 is formed from multiple components including perforator/spike 30, a shell 50, a compression spring 70 and an actuator or slider 80. Any of valve 20, perforator/spike 30, shell 50, and/or actuator or slider 80 of perforating connector assembly 10 may be formed, e.g., molded, from a thermoplastic, such as polyetherimide ("PEI"), polyethersulfone ("PES"), polyamide/nylon ("PA"), acrylonitrile butadiene styrene ("ABS"), polycarbonate ("PC") polyetheretherketone ("PEEK"), or polyvinylchloride ("PVC"). Valve 20 and/or a separate o-ring if provided may be formed, e.g., molded, alternatively from an elastomer, such as ethylene propylene diene monomer ("EPDM") rubber, neoprene rubber, silicon rubber, thermo-plastic vulcunizates ("TPVs") or thermosplastic elastomers ("TPEs"). Compression spring 70 may be formed from a material configured to provide a desired spring force including, stainless steel, high carbon spring steels in wire or flat form, music wire, copper-based spring alloys, nickel-based spring alloys, and alloy spring steels such as chromium vanadium, silicon manganese and chromium silicon.

FIG. 1 illustrates that perforating connector assembly 10 in one embodiment includes valve 20 for operation with perforating connector 12, wherein valve 20 may be a flexible plastic or rubber piece that is welded, e.g., ultrasonically sealed, heat sealed, or solvent bonded to the medical fluid, e.g., PD fluid, bag 14. Valve 20 may be a cylindrical plastic or rubber piece that has a circular flanged bottom 22, for increasing the welding surface for fluid-tight sealing to bag 14. Valve 20 may be provided with one or more o-ring seal 24, e.g., at its distal end and/or at its base, for sealing and/or centering movement within an inner surface of shell 50. Although not illustrated, valve 20 may be provided alternatively or additionally on its inner surface with an inwardly extending o-ring seal for sealing to an outside diameter of perforator/spike 30.

Figure 2:
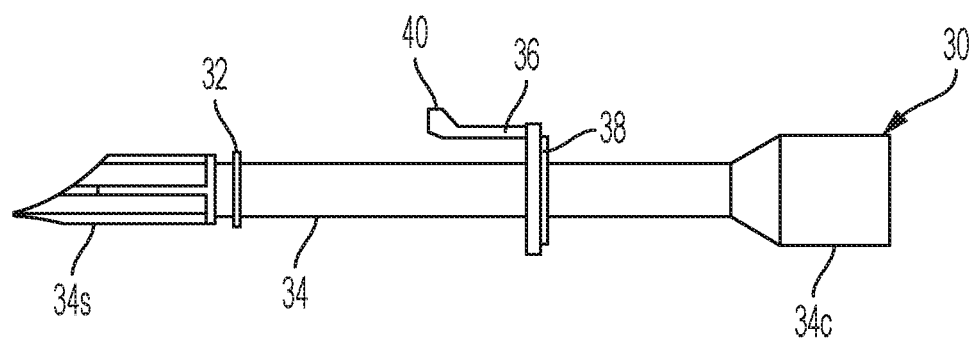
FIG. 2 is a side view of one embodiment of a perforator/spike of the perforating connector of the present disclosure.

FIG. 2 illustrates that perforating connector 12 includes perforator/spike 30 in one illustrated embodiment, which may be fitted or formed with an o-ring 32 that provides a sealed and moveable communication within valve 20, so that medical fluid, e.g., PD fluid, once accessed cannot flow from the PD fluid bag, within valve 20 and around the outside of perforator/spike 30. O-ring 32 may alternatively be a separate o-ring. Perforator/spike 30 is actuated within valve 20 to pierce medical fluid, e.g., PD fluid, bag 14 and access the medical, e.g., PD fluid.

Perforator/spike 30 in the illustrated embodiment includes an elongated cylindrical body 34 (to which o-ring 32 may be formed or attached). One end of cylindrical body 34 is a spiked end 34s, while the other end of cylindrical body 34 is formed with or attached to a connector 34c for connecting to a tube (not illustrated), such as a flexible tube for carrying medical fluid, e.g., PD fluid, from perforating connector 12. Connector 34c may be a threaded, e.g., luer, connector or be sized to permanently seal to the tube, e.g., via ultrasonically sealing, heat sealing, or solvent bonding.

A lever 36 extends from elongated tubular body 34, e.g., is molded with the tubular body. Lever 36 in the illustrated embodiment extends from a circular lever wall 38, which in turn extends from elongated tubular body 34. Lever 36 may be cantilevered to circular lever wall 38 so as to be able to bend downwardly or upwardly relative to tubular body 34. A tab 40 is provided at the end of lever 36 and extends radially outwardly in the illustrated embodiment.

Figure 3:
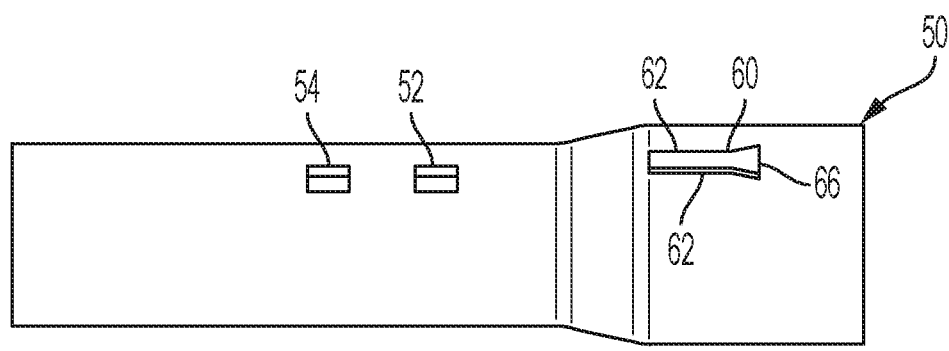
FIG. 3 is a side view of one embodiment of a shell of the perforating connector of the present disclosure.

FIG. 3 illustrates that perforating connector 12 further includes a shell 50, e.g., a cylindrical shell in the illustrated embodiment, which resides on the outside of valve 20 and perforator/spike 30 and centers/aligns movement of perforator/spike 30 within valve 20. Shell 50 is formed, e.g., molded, with a pair of openings 52, 54, including a pre-activation opening 52 and a post-activation opening 54.

Tab 40 of lever 36 of perforator/spike 30 resides initially (before activation) in pre-activation opening 52 of shell 50. Such engagement prevents perforator/spike 30 from moving or being moved relative to shell 50, valve 20 or medical fluid, e.g., PD fluid, bag 14. The second or post-activation opening 54 of shell 50 sets and end-of-travel location for perforator/spike 30. Tab 40 in the illustrated embodiment resides in post-activation opening 54 of shell 50 after activation (bag spiking).

Figure 4:
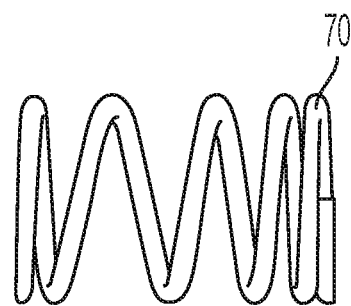
FIG. 4 is a side view of one embodiment of a spring of the perforating connector of the present disclosure.

FIG. 4 illustrates that perforating connector 12 in one embodiment includes a compression spring 70, which is compressed initially between circular lever wall 38 of perforator/spike 30 and an internal ledge 56 (FIGS. 6 to 8) of shell 50 provided at or near a distal end of the shell. Compression spring 70 is sized, e.g., with a coil diameter, and is made of a desired material such that the spring provides enough force upon decompression to cause perforator/spike 30 to pierce medical fluid, e.g., PD fluid, bag 14. When tab 40 on lever 36 of perforator/spike 30 is pushed beneath and out of the initial or pre-activation opening 52 of shell 50, compression spring 70 is able to uncoil and automatically translate the perforator/spike.

Figure 5:
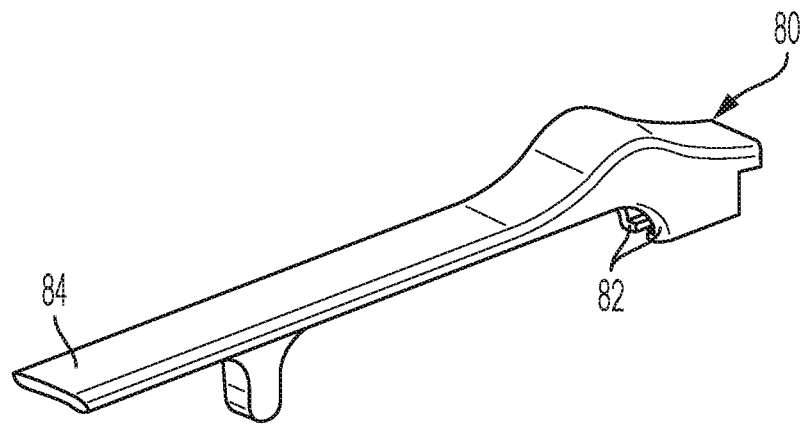
FIG. 5 is a perspective view of one embodiment of an actuator or slider of the perforating connector of the present disclosure.

FIG. 5 illustrates that perforating connector 12 of the present disclosure additionally includes an actuator or slider 80 that is press-fitted into and thus constrained by slots 62 provided in shell 50 of FIG. 3, so as to be able to only translate back and forth in one direction. Slots 62 are provided in the illustrated embodiment by a member 60 that extends radially outwardly from shell 50. Actuator or slider 80 may then include inwardly extending legs 82 that engage slots 62 formed by member 60 of shell 50. FIG. 3 illustrate that member 60 at one end angles out to a flared head 66, which makes an interference fit with slider 80 to hold the slider in place until actuation as discussed in detail in connection with FIG. 9.

Actuator or slider 80 in the illustrated embodiment is elongated so that its distal end 84 covers pre-activation opening 52 formed in shell 50 that houses outwardly extending tab 40 of lever 36 of perforator/spike 30 in the pre-actuated condition or state of assembly 10. In this manner, distal end 84 of actuator or slider 80 prevents (i) the user from prematurely actuating perforating connector assembly 10 and (ii) outwardly extending tab 40 from being moved prematurely, e.g., during shipping. Actuator or slider 80 is further provided, e.g., molded, with a downwardly extending projection 86, which extends from a middle or off-center portion of the actuator or slider. Downwardly extending projection 86 is used to push outwardly extending tab 40 of lever 36 inwardly from the pre-activation opening 52.

FIGS. 6 to 8 of perforating connector assembly 10 illustrate that actuator or slider 80 resides radially close to the outer diameter of shell 50. Actuator or slider 80 therefore does not present a big risk in becoming snagged or entangled with an outside structure, e.g., during shipping, which could disrupt perforating connector assembly 10, such as moving actuator or slider 80 relative to the rest of perforating connector 12.

Activation of spring-activated perforating connector assembly 10 occurs as follows in one embodiment. FIG. 6 illustrates that prior to activation, outwardly extending tab 40 supported by lever 36 of perforator/spike 30 resides within the pre-activation shell opening 52, which prevents the pre-coiled spring 70 from uncoiling and perforator/spike 30 from being translated relative to the rest of assembly 10. Here, spiked end 34s of perforator/spike 30 resides essentially at the base of valve 20. Important in one embodiment is that distal end 84 of actuator or slider 80 is extended so that it covers and shields tab 40 of perforator/spike 30 residing within the pre-activation shell opening 52 prior to activation, preventing premature activation.

FIG. 7 illustrates that during the activation of perforating connector assembly 10, the user touches and translates actuator or slider 80 so that its downwardly extending projection 86 meets the upwardly extending tab 40 of perforator/spike 30 residing within pre-activation shell opening 52. The user then presses slider 80 and projection 86 radially into pre-activation opening 52, which forces tab 40 of perforator/spike 30 out of the opening, which in turn allows compression spring 70 to uncoil and automatically translate perforator/spike 30, including lever 36, in a direction so that spiked end 34*s* of the perforator/spike pierces the medical fluid, e.g., PD fluid, bag 14 open, allowing access to the medical or PD fluid within. During activation, the uncoiling of compression spring 70 translates perforator/spike 30 until tab 40 on lever 36 of the perforator/spike meets the post-activation shell opening 54. When this happens, lever 36 which is biased to spring upwardly during activation automatically snaps upwardly into post-activation opening 54, preventing perforator/spike 30 from being translated further. It should be appreciated that compression spring 70 provides the piercing force needed to overcome the tear resistance of container or bag 14, so that the user does not have to provide such force.

FIG. 8 illustrates that after activation of perforating connector assembly 10, with the medical fluid, e.g., PD fluid, bag 14 punctured, medical or PD fluid may flow from the medical or PD fluid bag 14, through an internal lumen of perforator/spike 30, into a medical or PD treatment fluid line or tube (not illustrated) attached to connector 34*c* of the perforator/spike. Outwardly extending tab 14 of lever 36 of the of perforator/spike 30 remains within post-activation opening 54 of shell 54, so that the spiked end 34*s* of perforator/spike 30 is held fixedly within the medical fluid, e.g., PD fluid, bag 14 while the bag is emptied.

Figure 9:
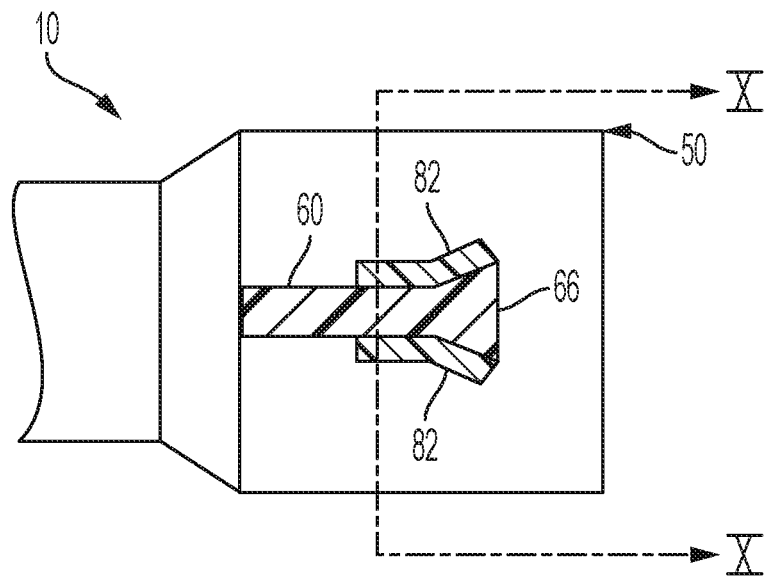
FIG. 9 is a top, partially sectioned view of one embodiment for an interference fit between the actuator and the member, wherein the actuator is held releasably in place during sterilization, handling, packing, transportation and storage prior to use.
Figure 10:
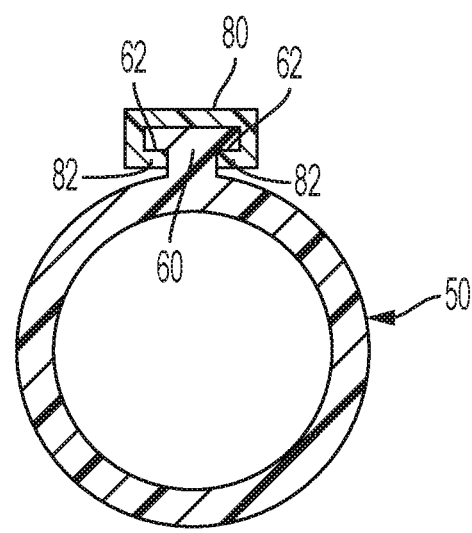
FIG. 10 is a sectioned end view taken along line XX of FIG. 9 illustrating one embodiment for slideably restraining the slider against the member of the shell.

FIGS. 9 and 10 illustrate one embodiment for an interference fit between actuator or slider 80 and member 60 of shell 50. FIGS. 3 and 5 illustrate that member 60 defines slots 62 (FIG. 3) that frictionally but slideably accept inwardly extending legs 82 (FIG. 5) of slider 80. FIG. 9 illustrates that member 60 may additionally be formed with or attached to a flared head 66, which angles out in a triangular manner from the remainder of member 60. Flared head 66 creates and interference fit with legs 82 of actuator or slider 80, preventing the actuator or slider from moving to the right or to the left in FIG. 9 prior to and during actuation. To actuate perforating connector assembly 10, the user presses slider 80 and slides it from right to left in FIG. 9 to overcome the holding force of the interference fit between flared head 66 and legs 82 of actuator or slider 80. Once legs 82 are slid to the left of the interference fit due to flared head 66, slider 80 may be slid further to the left without substantial interference. In one embodiment, legs 82 of slider 80 remain within slots 62 of member 60 over the entire course of travel for the member, so that its movement is always guided.

Although not illustrated in FIG. 9, member 60 may additionally be formed with projections/indentations, which temporarily extend into or accept mating indentations/projections formed in legs 82 of slider 80. The interference fit between the projections and indentations would additionally hold actuator or slider 80 releasably in place against member 60 during sterilization, handling, packing, transportation and storage prior to use. To actuate perforating connector assembly 10, the user would here press slider 80 and slide it from right to left in FIG. 9 to overcome the holding force of the interference fit between the projections and the indentations. Once legs 82 are slid to the left of the projection/indentation interference fit, slider 80 may be slid further to the left without substantial interference.

FIG. 10 illustrates an end view of actuator or slider 80 slidingly engaged to member 60 and further illustrates the structure and functionality described above in connection with FIGS. 3 and 5. In particular, member 60 defines slots 62 that receive legs 82 of actuator or slider 80 so that the slider may not come upwardly off of member 60. As discussed, legs 82 of slider 80 remain within slots 62 of member 60 over the entire course of travel for the member in one embodiment, so that slider 80 cannot come free from member 60 or shell 50 regardless of the location of slider 80 relative to member 60.

It should be understood that various changes and modifications to the presently preferred embodiments described herein will be apparent to those skilled in the art. It is therefore intended that any or all of such changes and modifications may be covered by the appended claims. For example, while o-ring 32 is illustrated as being fitted or formed with perforator/spike 30, the o-ring may be provided alternatively with valve 20.

The invention is claimed as follows:

1. A perforating connector assembly comprising:
   a valve for sealing to a medical fluid container; and
   a perforating connector comprising
   a perforator sealingly accepted by the valve, the perforator including a spiked end and a lever, the lever including a tab,
   a shell extending around the perforator sealingly accepted by the valve, the shell including a pre-activation opening and a post-activation opening,
   a spring held compressed during pre-activation by the tab of the lever of the perforator being located within the pre-activation opening of the shell, and
   an actuator slidingly engaged to the shell, the actuator including a projection, the actuator configured to be translated by a user so that the projection becomes aligned with the tab located within the pre-activation opening, wherein the user is then able to push the projection into the pre-activation opening to disengage the tab from the pre-activation opening, and wherein the spring is then able to decompress and translate the perforator so that the medical fluid container is pierced open by the spiked end and the tab becomes located within the post-activation opening.

2. The perforating connector assembly of claim 1, wherein the valve includes a flanged bottom for enhancing a weld between the valve and the medical fluid container.

3. The perforating connector assembly of claim 1, wherein the perforator is sealingly accepted by the valve via an o-ring, and wherein the o-ring is formed with the perforator, the valve, or is a separate o-ring.

4. The perforating connector assembly of claim 1, wherein an end of the perforator includes a connector for connecting to a tube configured to transport medical fluid from the medical fluid container.

5. The perforating connector assembly of claim 1, wherein the perforator includes an elongated cylindrical body and a circular wall extending from the body, wherein the lever extends from the circular wall, and wherein the spring is held compressed by the circular wall.

6. The perforating connector assembly of claim 5, wherein the shell includes an internal ledge, and wherein the spring is also held compressed by the internal ledge.

7. The perforating connector assembly of claim 1, wherein a distal end of the actuator is extended such that during pre-activation, the distal end covers the tab of the lever of the perforator located within the pre-activation opening of the shell.

8. The perforating connector assembly of claim 1, wherein the tab extends radially outwardly from the lever into the pre- and post-activation openings.

9. The perforating connector assembly of claim 1, wherein the lever is bent by the tab contacting an inner surface of the shell while the lever is moved between the pre- and post-activation openings, the bending of the lever biasing the lever to snap into the post-activation opening upon reaching the post-activation opening.

10. The perforating connector assembly of claim 1, wherein the projection extends radially inwardly from the actuator to allow the user to push the projection into the pre-activation opening to disengage the tab from the pre-activation opening.

11. The perforating connector assembly of claim 1, wherein the shell includes an outwardly extending member defining at least one slot, and wherein the actuator includes at least one leg configured to engage the at least one slot so that the actuator is constrained to translate relative to the shell.

12. A perforating connector comprising:
a perforator including a spiked end and a lever, the lever including a tab;
a shell extending around the perforator, the shell including a pre-activation opening and a post-activation opening;
a spring held compressed during pre-activation by the tab of the lever of the perforator being located within the pre-activation opening of the shell; and
an actuator slidingly engaged to the shell, the actuator including a projection, the actuator configured to be translated by a user so that the projection becomes aligned with the tab located within the pre-activation opening, wherein the user is then able to push the projection into the pre-activation opening to disengage the tab from the pre-activation opening, and wherein the spring is then able to decompress and translate the perforator so that a medical fluid container is pierced open by the spiked end and the tab becomes located within the post-activation opening.

13. The perforating connector of claim 12, wherein the actuator resides radially adjacent to the shell, such that the actuator is prone not to become entangled with an outside structure.

14. The perforating connector of claim 12, wherein at least one of a coil diameter and a material of the spring are selected so that the spring provides enough force for the medical fluid container to be pierced open by the spiked end of the perforator.

15. The perforating connector of claim 12, wherein the projection is provided at a middle or off-center portion of the actuator.

16. A method for accessing a medical fluid, the method comprising:
providing a perforator including a spiked end and a lever, the lever including an outwardly extending tab;
providing a shell extending around the perforator, the shell including an opening holding the tab of the lever prior to accessing the medical fluid;
providing a spring that is compressed by the perforator and the shell prior to accessing the medical fluid; and
providing an actuator that enables a user to translate the actuator relative to the shell so that an inwardly extending projection of the actuator comes into registry with the tab of the lever held in the opening of the shell, wherein the user is able to push the actuator so that the projection removes the tab from the opening, allowing the spring to decompress and translate the perforator so that a medical fluid container is pierced open by the perforator.

17. The method of claim 16, which includes providing a valve with the medical fluid container, wherein the perforator moves sealingly within the valve.

18. The method of claim 17, wherein the shell extends around an outside of the valve.

19. The method of claim 16, wherein the medical fluid container is a peritoneal dialysis ("PD") fluid container.

20. The method of claim 16, which includes preventing the actuator from being translated relative to the shell in a non-registry direction and releasably preventing the actuator from being translated relative to the shell in a registry direction.

* * * * *